(12) United States Patent
Bettuchi et al.

(10) Patent No.: US 9,028,528 B2
(45) Date of Patent: *May 12, 2015

(54) SEAL ELEMENT FOR ANASTOMOSIS

(71) Applicant: Covidien LP, Mansfield, MA (US)

(72) Inventors: Michael J. Bettuchi, Middletown, CT (US); David N. Fowler, Chesire, CT (US); Ahmad Robert Hadba, Forth Worth, TX (US); Christopher J. Criscuolo, Branford, CT (US); John J. Kennedy, Guilford, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/185,162

(22) Filed: Feb. 20, 2014

(65) Prior Publication Data

US 2014/0166719 A1 Jun. 19, 2014

Related U.S. Application Data

(63) Continuation of application No. 13/738,076, filed on Jan. 10, 2013, now Pat. No. 8,663,258, which is a continuation of application No. 12/841,581, filed on Jul. 22, 2010, now Pat. No. 8,236,015, which is a continuation of application No. 11/238,497, filed on Sep. 28, 2005, now Pat. No. 8,372,094.

(60) Provisional application No. 60/619,238, filed on Oct. 15, 2004.

(51) Int. Cl.
*A61B 17/03* (2006.01)
*A61B 17/068* (2006.01)
*A61B 17/072* (2006.01)
*A61B 17/115* (2006.01)
*A61B 17/11* (2006.01)

(52) U.S. Cl.
CPC .............. *A61B 17/068* (2013.01); *A61B 17/072* (2013.01); *A61B 17/07292* (2013.01); *A61B 17/115* (2013.01); *A61B 17/1155* (2013.01); *A61B 2017/07214* (2013.01); *A61B 17/11* (2013.01)

(58) Field of Classification Search
CPC .............. A61B 17/068; A61B 17/072; A61B 17/07292; A61B 17/11; A61B 17/1114; A61B 17/115; A61B 17/1155; A61B 2017/07214; A61B 2017/07221; A61B 2017/07257; A61B 2017/1103; A61B 2017/1107; A61B 2017/1125; A61B 2017/1132
USPC ..................... 606/153–155; 227/175.1, 179.1
See application file for complete search history.

(56) References Cited

U.S. PATENT DOCUMENTS 3,054,406 A 9/1962 Usher
3,124,136 A 3/1964 Usher (Continued)

FOREIGN PATENT DOCUMENTS

| DE | 199 24 311 A1 | 11/2000 |
|---|---|---|
| EP | 1 256 317 A2 | 11/2002 |
| WO | WO 03/105698 A2 | 12/2003 |

OTHER PUBLICATIONS

International Search Report and Written Opinion corresponding to International Application No. PCT/US05/35120 dated, May 6, 2008 (10 pages).

(Continued)

*Primary Examiner* — Ryan Severson

(57) ABSTRACT

A seal element for sealing between tissue lumens includes a first material for allowing tissue ingrowth and a second sealant material.

18 Claims, 4 Drawing Sheets

(56) References Cited

U.S. PATENT DOCUMENTS

| | | | |
|---|---|---|---|
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,788,979 A | 12/1988 | Jarrett et al. | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,124,103 A | 6/1992 | Kaplan et al. | |
| 5,222,963 A | 6/1993 | Brinkerhoff et al. | |
| 5,263,629 A | 11/1993 | Trumbull et al. | |
| 5,314,471 A | 5/1994 | Brauker et al. | |
| 5,344,454 A | 9/1994 | Clarke et al. | |
| 5,392,979 A | 2/1995 | Green et al. | |
| 5,397,324 A | 3/1995 | Carroll et al. | |
| 5,423,859 A | 6/1995 | Koyfman et al. | |
| 5,425,745 A | 6/1995 | Green et al. | |
| 5,441,193 A | 8/1995 | Gravener | |
| 5,468,253 A | 11/1995 | Bezwada et al. | |
| 5,503,638 A | 4/1996 | Cooper et al. | |
| 5,542,594 A | 8/1996 | McKean et al. | |
| 5,543,218 A | 8/1996 | Bennett et al. | |
| 5,549,628 A | 8/1996 | Cooper et al. | |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,716,376 A | 2/1998 | Roby et al. | |
| 5,752,965 A | 5/1998 | Francis et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,774 A | 10/1999 | McKean et al. | |
| 5,997,895 A | 12/1999 | Narotam et al. | |
| 6,019,791 A | 2/2000 | Wood | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,165,185 A | 12/2000 | Shennib et al. | |
| 6,210,439 B1 | 4/2001 | Firmin et al. | |
| 6,214,020 B1 | 4/2001 | Mulhauser et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,503,259 B2 | 1/2003 | Huxel et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 2002/0016626 A1 | 2/2002 | DiMatteo et al. | |
| 2002/0019187 A1 | 2/2002 | Carroll et al. | |
| 2002/0052622 A1 | 5/2002 | Rousseau | |
| 2002/0091397 A1 | 7/2002 | Chen | |
| 2002/0133236 A1 | 9/2002 | Rousseau | |
| 2002/0138152 A1 | 9/2002 | Francis et al. | |
| 2002/0151911 A1 | 10/2002 | Gabbay | |
| 2002/0165559 A1 | 11/2002 | Grant et al. | |
| 2002/0165562 A1 | 11/2002 | Grant et al. | |
| 2002/0165563 A1 | 11/2002 | Grant et al. | |
| 2003/0065345 A1 | 4/2003 | Weadock | |
| 2003/0065346 A1 | 4/2003 | Evens et al. | |
| 2003/0083676 A1 | 5/2003 | Wallace | |
| 2003/0105510 A1 | 6/2003 | DiMatteo et al. | |
| 2003/0114866 A1 | 6/2003 | Ulmsten et al. | |
| 2003/0167064 A1 | 9/2003 | Whayne | |
| 2003/0181927 A1 | 9/2003 | Wallace | |
| 2003/0183671 A1 | 10/2003 | Mooradian et al. | |
| 2004/0034377 A1 | 2/2004 | Sharkawy et al. | |
| 2004/0092960 A1 | 5/2004 | Abrams et al. | |
| 2004/0093029 A1 | 5/2004 | Zubik et al. | |
| 2004/0107006 A1 | 6/2004 | Francis et al. | |
| 2004/0116945 A1 | 6/2004 | Sharkawy et al. | |
| 2004/0142621 A1 | 7/2004 | Carroll et al. | |
| 2004/0172048 A1 | 9/2004 | Browning | |
| 2004/0209059 A1 | 10/2004 | Foss | |
| 2004/0215214 A1 | 10/2004 | Crews et al. | |
| 2004/0215219 A1 | 10/2004 | Eldridge et al. | |
| 2004/0215221 A1 | 10/2004 | Suyker et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1 | 1/2005 | Baily | |
| 2005/0021053 A1 | 1/2005 | Heinrich | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0118435 A1 | 6/2005 | DeLucia et al. | |

OTHER PUBLICATIONS

European Search Report corresponding to European Application No. EP 05803193.1-2310 dated, Feb. 9, 2010 (3 pages).

Cross-Section of Circular Anastomosis

SEAL ELEMENT FOR ANASTOMOSIS

CROSS-REFERENCE TO RELATED APPLICATIONS

The instant patent application is a Continuation Application which claims the benefit of and priority to U.S. patent application Ser. No. 13/738,076 filed on Jan. 10, 2013, now U.S. Pat. No. 8,663,258, which claims the benefit of and priority to U.S. patent application Ser. No. 12/841,561 filed on Jul. 22, 2010, now U.S. Pat. No. 8,236,015, which claims the benefit of and priority to U.S. patent application Ser. No. 11/238,497 filed on Sep. 28, 2005, now U.S. Pat. No. 8,372,094, which claims the benefit of and priority to U.S. Provisional Patent Application Ser. No. 60/619,238 filed on Oct. 15, 2004, the entire disclosures of which are incorporated herein by reference.

BACKGROUND

1. Technical Field

The present disclosure relates to devices for attaching two tubular tissues. More particularly, seals for use in connection with anastomosis procedures are described.

2. Background of Related Art

One method for performing a gastrointestinal anastomosis involves the use of a circular stapler apparatus. For example, a device known as the CEEA® (trademark of United States Surgical, a division of Tyco Healthcare Group LP) is utilized after resection of a diseased portion of bowel. The circular anastomosis stapler is utilized to approximate the remaining portions of bowel, staple them together, and cut away excess tissue at the anastomotic joint.

Illustrative circular stapling devices are disclosed in certain embodiments of U.S. Pat. Nos. 4,354,628; 5,014,899; 5,040,715; and 5,392,979 the disclosures of which are hereby incorporated herein in their entirety by this reference. Other methods of performing anastomoses, utilizing joining techniques other than stapling that have been contemplated include, for example the use of clip appliers, dissectors and shears, and adhesives.

While present anastomosis devices and procedures perform satisfactorily, it would be advantageous to promote tissue growth and good sealing at an anastomosis site.

SUMMARY

A composite seal element for use in anastomosis is described herein. The seal element can be disposed between the two portions of tubular tissue to be joined to promote tissue growth and reduce the occurrence of leaks. In stapled anastomoses, the seal element is disposed between the proximal and distal ends of an anastomosis before the tissue is approximated and staples are fired. The seal element remains in place during the healing process and then, in certain embodiments is absorbed by the body.

One aspect of the present disclosure is a seal element for sealing between tissue lumens, comprising a first material and a second material. The first material comprises a porous material for allowing tissue ingrowth. The second material comprises a sealant.

In embodiments, the second material comprises a compressible material that, when compressed between a first tissue lumen and a second tissue lumen, acts as a seal to prevent the escape of the contents of the tissue lumens. Preferably, the first material and the second material are biodegradable, bioabsorbable, or bioresorbable materials.

In certain embodiments, the seal element comprises an annular element and the second material is disposed outwardly of the first material. The first and second materials may be adhered to one another, with a biocompatible adhesive, or joined utilizing an overmolding process.

Another aspect of the present disclosure is an assembly for disposing a seal element between tissue lumens comprising a circular surgical stapling device, having an anvil assembly and a tubular body portion, the anvil assembly having an anvil member and a first shaft, the tubular body portion carrying a plurality of surgical staples in a circular configuration, the tubular body portion having a second shaft disposed inwardly of the surgical staples, the first shaft being attachable to the second shaft. The assembly includes a seal element comprising a first material and a second material. The first material comprises a porous material for allowing tissue ingrowth. The second material comprises a sealant.

Preferably, the second material comprises a compressible material that, when compressed between a first tissue lumen and a second tissue lumen, acts as a seal to prevent the escape of the contents of the tissue lumens. Preferably, the first material and the second material are biodegradable, bioabsorbable, or bioresorbable materials.

The seal element desirably has a generally centrally located aperture for being disposed on one of the first shaft and the second shaft of the circular surgical stapling device.

In some embodiments the seal element having an inner disc of a first material and an outer disc of a second material wherein the first material promotes tissue ingrowth and the second material comprises a sealant, the first material extending into the second material.

BRIEF DESCRIPTION OF THE DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein.

DETAILED DESCRIPTION OF PREFERRED EMBODIMENTS

Figure 1:
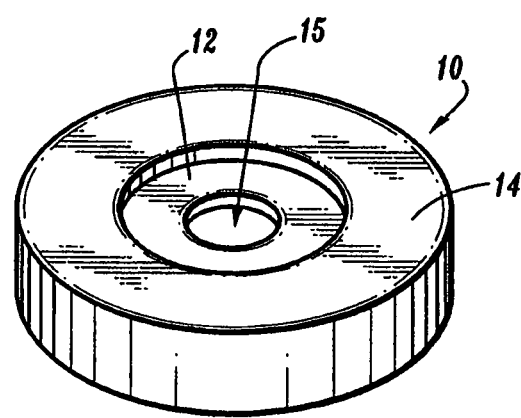
FIG. 1 is a perspective view of a seal element in accordance with an embodiment of the present disclosure, shown in an undeployed condition.

As shown in FIG. 1, a seal element 10 in accordance with the present disclosure can be a composite of a first material 12 and a second material 14, and includes a center aperture 15.

In certain embodiments, the first material 12 can be relatively thin (compared to the second material) and optionally is a bioabsorbable material that promotes tissue ingrowth. In certain preferred embodiments, first material 12 can be about 0.010" to about 0.020" thick, although other thicknesses can be used. As those skilled in the art will appreciate, tissue ingrowth is promoted more readily by materials having pores formed therein. Thus, for example, first material 12 can be any biocompatible, optionally bioabsorbable porous material, such as, for example, a foam, a mesh, a non-woven structure, or a perforated sheet. In certain preferred embodiments, first material 12 has pores in the range of about 50 μm to about 200 μm. Illustrative examples of suitable bioabsorbable porous materials include an absorbable hernia mesh such as Dexon, an absorbable felt such as Polysorb, or a porous open-cell foam such as polyurethane, suitable homopolymers, glycolide, lactide, caprolactone, trimethylene carbonate, dioxanone, polyalkylene oxides, etc. Other suitable materials are disclosed in certain embodiments of U.S. Pat. Nos. 4,655,221; 4,788,979; 5,543,218; 5,716,376; 5,423,859; and 5,124,103, the disclosures of which are hereby incorporated herein in their entirety by this reference. Without being limited to a particular theory of operation, there is a considerable amount of healing that takes place in this region. Therefore, this material is desirably porous enough to allow tissue to grow through it.

The second material 14 desirably forms a seal. Thus, second material 14 can be, for example, either a compressible or expandable optionally bioabsorbable material. In use, compressible second materials 14, when compressed, act as a seal to prevent the escape of fluid from the connected tubular tissue. In some embodiments, second material 14 is a soft, compliant material that is compressed between the proximal 16 and distal ends 18 of the anastomosis and captured by staples 33, 35. See, e.g., FIG. 4. The compression of this material can serve, for example, as a gasket to prevent bowel contents from leaking into the peritoneum. Illustrative examples of compressible materials include, but are not limited to polyurethane foam, carboxymethyl cellulose ("CMC"), and hydrogels.

For expandable second materials 14, the material may expand in response to contact with fluids, such as the fluids naturally present in the body. In embodiments, second material 14 can be a de-hydrated material that swells upon contact with moisture. For example, second material 14 can be a hydrophilic biomaterial. Illustrative examples of suitable hydrophilic biomaterials include, but are not limited to polymers formed from one or more of the following monomers: methacrylic acid, acrylic acid, n-vinyl pyrrolidone, potassium sulfopropyl acrylate, potassium sulfopropyl methacrylate, acrylamide, dimethylacrylamide, 2-methacryloyloxyethyl phosphorylcholine, 2-hydroxyethyl methacrylate or similar biocompatible water-soluble vinyl monomers. In a particularly useful embodiment, second material 14 is formed of poly(2-hydroxyethyl methacrylate). Where seal element 10 includes a hydrophilic biomaterial as second material 14, seal element 10 can be prepared using techniques within the purview of those skilled in the art. For example, the seal element can be formed by filling a mold with a composition containing the monomer(s) and, if desired or necessary, initiator, crosslinker, plasticizer and/or biological agent, and polymerizing the composition within the mold. The choice of particular initiators, crosslinkers, etc. will be determined by the specific choice of monomer(s) and can be readily determined by those skilled in the art. A particularly useful hydrophilic biomaterial is poly(2-hydroxyethyl methacrylate) ("PHEMA"). The equilibrium water content (EWC), swelling, and mechanical properties of the PHEMA portion of seal element 10 can be controlled by crosslink density (e.g., the crosslink density can be controlled by radiation conditions or crosslinking agent, such as di(ethylene glycol) dimethacrylate (DEGDMA), concentration). The thickness of the seal element 10 is controlled by the volume of the monomer composition polymerized in the mold. The PHEMA portion of seal element 10 can also be surface modified following formation. For example, the PHEMA portion of seal element 10 can be surface modified with polymeric phospholipids for improved hemocompatibility and tissue interaction using gamma radiation grafting.

In embodiments, the surface of the portion of the seal element made from second material 14 can be patterned or templated in the nano-meso-micro scale to accommodate preferential tissue interaction at the tissue/seal interface. Such architecture or patterns can prevent or minimize post-operative tissue adhesions and superfluous collagen deposition, but afford desired mechanical and biophysical support for wound healing.

Either or both of first material 12 and second material 14 from which seal element 10 is made may also contain one or more medically and/or surgically useful substances such as drugs, enzymes, growth factors, peptides, proteins, dyes, diagnostic agents or hemostasis agents or any other pharmaceutical used in the prevention of stenosis. Non-limiting examples of suitable medically and/or surgically useful substances include: antimicrobials, antibiotics, anti-fungals, anti-virals, monoclonal antibodies, polyclonal antibodies, antimicrobial proteins/peptides (whole and fragments), enzymes, gene therapy, viral particles, chemotherapeutics, anti-inflammatories, NSAIDS, steroids, telomerase inhibitors, growth factors (TGF family, interleukin superfamily, fibroblast derived GFs, macrophage derived GFs, etc.), extracellular matrix molecules (laminin, thrombospondin, collagen, fibronectin, synthetic ECM, etc.), cell adhesion molecules, polysaccharides (hyaluronic acid, carboxymethyl cellulose, alginate, sulfonated dextran, heparin sulfate, chitosan, etc.) and others. These agents can be incorporated in situ into either or both of first material 12 and second material 14 from which seal element 10 is made or post loaded onto seal element 10 using techniques within the purview of those skilled in the art. For example, the medically and/or surgically useful substances can be freely mixed or loaded, electronically or ionically bound, covalently immobilized, chelated, or encapsulated in particles, micelles, aggregates, or any nano-meso-micro solids of varied dimension, shape morphology and dispersion/suspension ability.

Second material 14 can be attached to first material 12 in any manner within the purview of those skilled in the art, including, but not limited to an overmolding process.

Seal element 10 desirably has a generally centrally located aperture 15 for being disposed on one of the first shaft and the second shaft of a circular surgical stapling device. The seal element is captured between the proximal and distal ends of a circular, stapled anastomosis to reduce leaks at the site of anastomosis.

The dimensions of seal element 10 may vary, according to the particular application. In certain embodiments, the outside diameter is slightly larger than the diameter of the outside staple row of the circular stapling apparatus. The inside diameter will be slightly larger than the diameter of the knife of the circular stapling apparatus. Preferably, the inside diameter may be about the size of shaft 38 of anvil assembly 40 in order to center seal element 10 on the anvil assembly 40.

Figure 2:
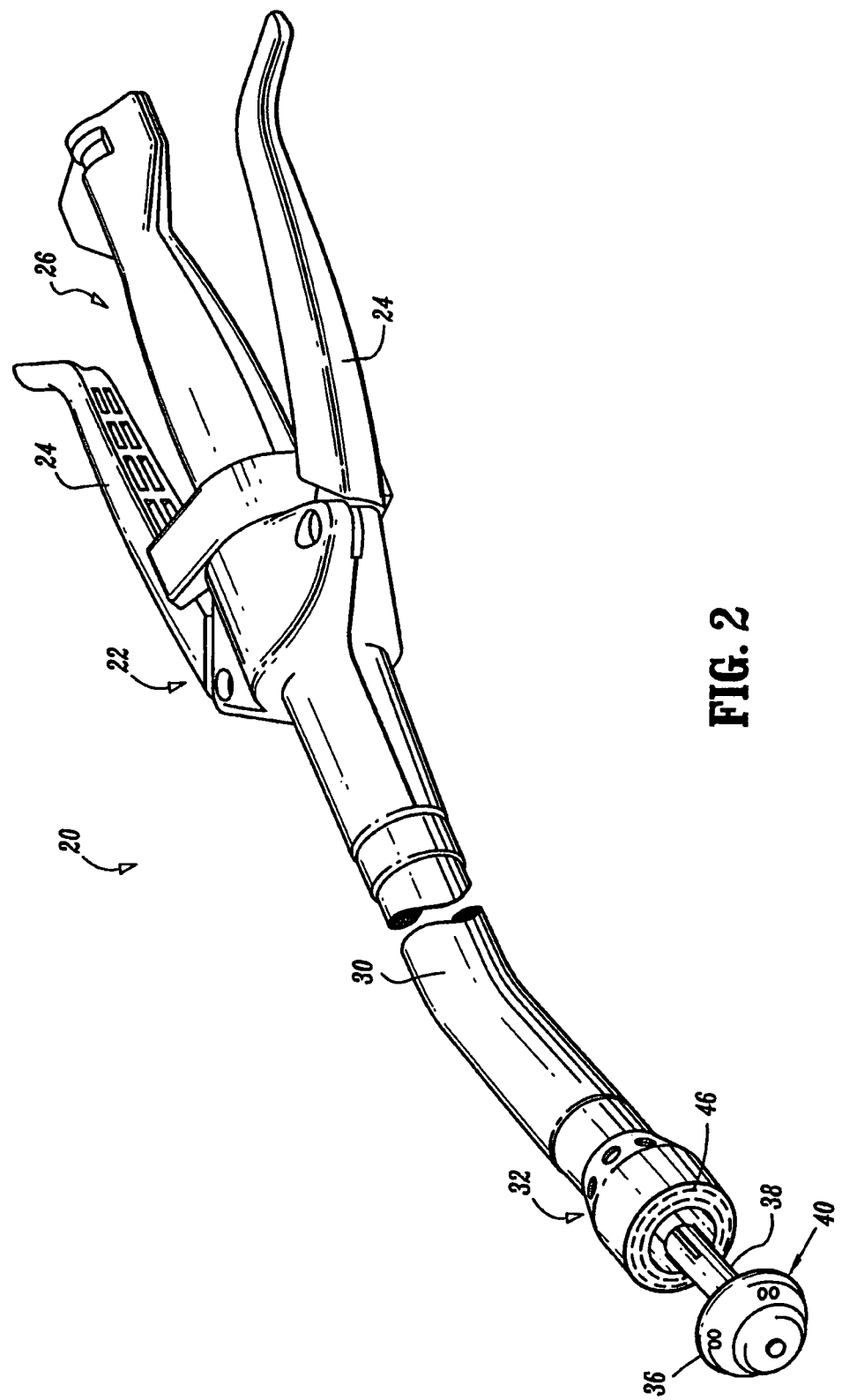
FIG. 2 is a perspective view of an exemplary annular surgical stapling device.

Referring now to FIG. 2, an annular surgical stapling device, for use with the annular structures disclosed herein, is generally designated as 20. Surgical stapling device includes a handle assembly 22 having at least one pivotable actuating handle member 24, and an advancing member 26. Extending from handle member 22, there is provided a tubular body portion 30 which may be constructed so as to have a curved shape along its length. Body portion 30 terminates in a staple cartridge assembly 32 which includes a pair of annular arrays of staple receiving slots 46 having a staple (not shown) disposed in each one of staple receiving slots 46. Positioned distally of staple cartridge assembly 32 there is provided an anvil assembly 40 including an anvil member 36 and a shaft 38 operatively associated therewith for removably connecting anvil assembly 40 to a distal end portion of the stapling device.

Staple cartridge assembly 32 may be fixedly connected to the distal end of tubular body portion 30 or may be configured to concentrically fit within the distal end of tubular body portion 30. Typically, staple cartridge assembly 32 includes a staple pusher (not shown) including a proximal portion having a generally frusto-conical shape and a distal portion defining two concentric rings of peripherally spaced fingers (not shown), each one of which is received within a respective staple receiving slot 46.

Typically, a knife (not shown), substantially in the form of an open cup with the rim thereof defining a knife edge, is disposed within staple cartridge assembly 32 and mounted to a distal surface of a staple pusher (not shown). The knife edge is disposed radially inward of the pair of annular arrays of staples. Accordingly, in use, as the staple pusher is advanced, the knife is also advanced axially outward.

Figure 3:
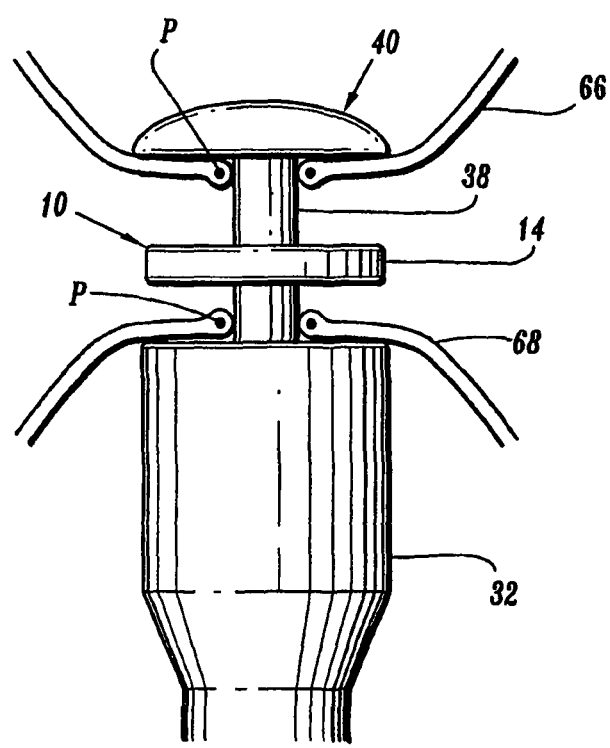
FIG. 3 is a longitudinal, partially cross-sectional view illustrating the anvil rod mounted to the annular stapling device within a surgical site and the seal element of FIG. 1 in an undeployed condition, disposed between the apposed surfaces of the tissue.

Reference may be made to U.S. Pat. No. 5,915,616 to Viola et al., the entire content of which is incorporated herein by reference, for a detailed discussion of a suitable annular stapling device. Although the stapling device shown in FIGS. 2-3 is a circular stapling device, the seal element disclosed herein may be used with staplers of other shapes or configurations, such as, for example, linear staplers or annular staplers that are not circular. In addition, the seal element may be placed using sutures, adhesives, etc.

Turning now to FIG. 3, there is illustrated the use of surgical stapling device 20 and detachable anvil assembly 40 in an anastomosis procedure to effect joining of intestinal sections 66 and 68. At the point in the procedure shown in FIG. 3, a diseased intestinal section has been previously removed, anvil assembly 40 has been applied to the operative site either through a surgical incision or transanally and positioned within intestinal section 66, and tubular body portion 30 of the surgical stapling device has been inserted transanally into intestinal section 68. Intestinal sections 66 and 68 are also shown temporarily secured about their respective components (e.g., shaft 38 of anvil assembly 40, and the distal end of tubular body portion 30) by conventional means such as a purse string suture "P".

According to one method, as seen in FIG. 3, if desired or if the surgical procedure requires, seal element 10 may be placed onto shaft 38 of anvil assembly 40 prior to the coupling of anvil assembly 40 to the distal end of tubular body portion 30. Following positioning of seal element 10 onto shaft 38 of anvil assembly 40, the surgeon maneuvers anvil assembly 40 until the proximal end of shaft 38 is inserted into the distal end of tubular body portion 30 of surgical stapling device 20, wherein the mounting structure (not shown) within the distal end of tubular body portion 30 engages shaft 38 to effect the mounting. Thereafter, anvil assembly 40 and tubular body portion 30 are approximated to approximate intestinal sections 66, 68 and capture seal element 10 therebetween. The surgical stapling device 20 is then fired thereby stapling intestinal sections 66, 68 to one another and cutting the portion of tissue and seal element 10 disposed radially inward of the knife, to complete the anastomosis.

Figure 4:
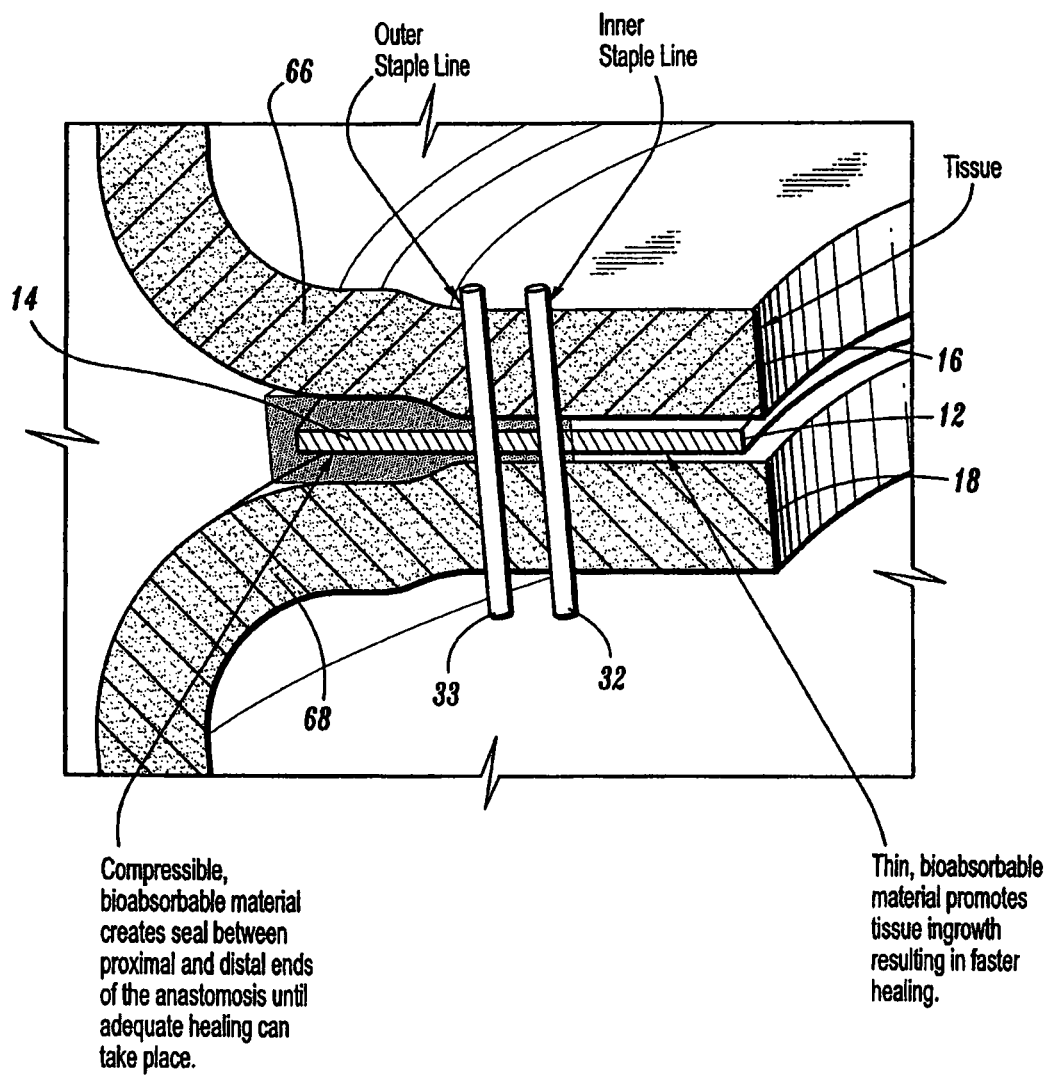
FIG. 4 is a perspective, cross sectional view of the seal element of FIG. 1 shown in a deployed condition.

As seen in FIG. 4, the seal forming second material 14 is compressed between the proximal 16 and distal ends 18 of the anastomosis and captured by the staples 33, 35. The compression of this material serves as a gasket to prevent bowel contents from leaking into the peritoneum. The portion of seal element 10 made from first material 12 is exposed at the site of anastomosis and serves to promote tissue ingrowth and thereby assist in healing of the site.

While several particular forms of the seal elements have been illustrated and described, it will also be apparent that various modifications can be made without departing from the spirit and scope of the present disclosure. For example, it is envisioned that each of the seal elements described herein may be used with an annular surgical anastomosing device, not including any staples for securing tissue together, which is capable of approximating, adhering and cutting tissue. Thus, it should be understood that various changes in form, detail and application of the support structures of the present disclosure may be made without departing from the spirit and scope of the present disclosure.

What is claimed is:

1. An assembly for disposing a seal element between tissue lumens comprising:
    a circular surgical stapling device comprising an anvil assembly and a tubular body portion wherein the anvil assembly comprises an anvil member and a first shaft and the tubular body portion comprises a plurality of surgical staples in a circular configuration and a second shaft disposed inwardly of the surgical staples, the first shaft being attachable to the second shaft; and
    a seal element disposable between the tissue lumens, the seal element comprising an inner first material comprising pores and an outer second material which expands upon contact with fluids, wherein the outer second material at least partially overlaps the inner first material.

2. The assembly of claim 1 wherein the inner first material extends into the outer second material.

3. The assembly of claim 1 wherein the inner first material is thinner than the outer second material.

4. The assembly of claim 3 wherein the inner first material is about 0.010" to about 0.020" thick.

5. The assembly of claim 1 wherein the inner first material comprises pores ranging in size from about 50 µm to about 200 µm.

6. The assembly of claim 1 wherein the inner first material is bioabsorbable.

7. The assembly of claim 1 wherein the inner first material is a foam.

8. The assembly of claim 1 wherein the inner first material is a mesh.

9. The assembly of claim 1 wherein the inner first material is a perforated sheet.

10. The assembly of claim 1 wherein the outer second material comprises poly(2-hydroxyethyl methacrylate).

11. The assembly of claim 1 further comprising a central aperture.

12. The assembly of claim 11 wherein a diameter of the central aperture is about the same size as a diameter of the first shaft.

13. The assembly of claim 11 wherein a diameter of the central aperture is slightly larger than a diameter of a knife of the circular surgical stapling device.

14. The assembly of claim 1 wherein at least one of the inner first material and the outer second material further comprises at least one medically useful substance.

15. The assembly of claim 1 wherein the outer second material is connected to the inner first material via adhesive.

16. The assembly of claim 1 wherein the outer second material is connected to the inner first material via an overmold.

17. The assembly of claim 1 wherein the inner first material comprises an inner disc shape.

18. The assembly of claim 17 wherein the outer second material comprises an outer disc shape.

* * * * *